(12) United States Patent
Shoberg et al.

(10) Patent No.: US 7,289,846 B2
(45) Date of Patent: Oct. 30, 2007

(54) MULTI-LUMEN MEDICAL ELECTRICAL LEAD BODY

(75) Inventors: Bret R. Shoberg, Corcoran, MN (US); Jordon D. Honeck, Maple Grove, MN (US)

(73) Assignee: Medtronic, Inc., Minneapolis, MN (US)

( * ) Notice: Subject to any disclaimer, the term of this patent is extended or adjusted under 35 U.S.C. 154(b) by 558 days.

(21) Appl. No.: 10/630,514

(22) Filed: Jul. 30, 2003

(65) Prior Publication Data

US 2005/0027342 A1 Feb. 3, 2005

(51) Int. Cl.
*A61N 1/05* (2006.01)

(52) U.S. Cl. .............. 607/2; 607/116; 607/119

(58) Field of Classification Search ........ 600/372, 600/373, 377, 393; 607/115, 116, 117, 122
See application file for complete search history.

(56) References Cited

U.S. PATENT DOCUMENTS

| | | | |
|---|---|---|---|
| 5,246,016 A * | 9/1993 | Lieber et al. ........... 128/898 |
| 5,303,704 A | 4/1994 | Molacek et al. ......... 128/642 |
| 5,324,321 A | 6/1994 | Pohndorf et al. | |
| 5,584,873 A | 12/1996 | Shoberg et al. ......... 607/122 |
| 5,871,530 A * | 2/1999 | Williams et al. ......... 607/122 |
| 5,882,346 A | 3/1999 | Pomeranz et al. ....... 604/280 |
| 5,957,970 A | 9/1999 | Shoberg et al. ......... 607/722 |
| 6,146,354 A | 11/2000 | Beil ....................... 604/28 |
| 2001/0044646 A1 | 11/2001 | Marshall et al. ......... 607/127 |
| 2002/0193860 A1 | 12/2002 | Bischoff et al. ......... 607/122 |

* cited by examiner

*Primary Examiner*—George Evanisko
*Assistant Examiner*—Michael Kahelin
(74) *Attorney, Agent, or Firm*—Michael C. Soldner; Carol F. Barry; Girma Wolde-Michael

(57) ABSTRACT

A medical electrical lead includes an elastomeric multi-lumen tube, which includes a lumen having a substantially elliptical cross-section through which a conductor having a substantially circular cross-section may extend. The substantially elliptical cross-section of the lumen includes a minor axis having a first length and being deformable such that the first length of the minor axis extends to a second length.

42 Claims, 6 Drawing Sheets

MULTI-LUMEN MEDICAL ELECTRICAL LEAD BODY

TECHNICAL FIELD

Embodiments of the present invention relate to medical electrical leads and more particularly to multi-lumen lead bodies.

BACKGROUND OF THE INVENTION

Implantable medical devices have long utilized medical electrical leads including elongated lead bodies, which carry one or more conductors coupling stimulation and or sensing electrodes or other types of sensors positioned at a target site to a connector coupled to a pulse generator or diagnostic device.

In order to carry out multiple functions, it is often desirable for a single lead body to carry multiple insulated conductors; however, it is also desirable for the lead body to have as small a profile or diameter as possible, to be flexible for implantation within a body, and to withstand damage under implant-environmental loading. These requirements may be addressed through the implementation of insulative multi-lumen tubing; embodiments presented herein exemplify novel configurations of multi-lumen tubing and arrangements of conductors therein.

BRIEF DESCRIPTION OF THE DRAWINGS

The following drawings are illustrative of particular embodiments of the invention and therefore do not limit its scope, but are presented to assist in providing a proper understanding of the invention. The drawings are not to scale (unless so stated) and are intended for use in conjunction with the explanations in the following detailed description. The present invention will hereinafter be described in conjunction with the appended drawings, wherein like numerals denote like elements, and.

DETAILED DESCRIPTION

Figure 1A:
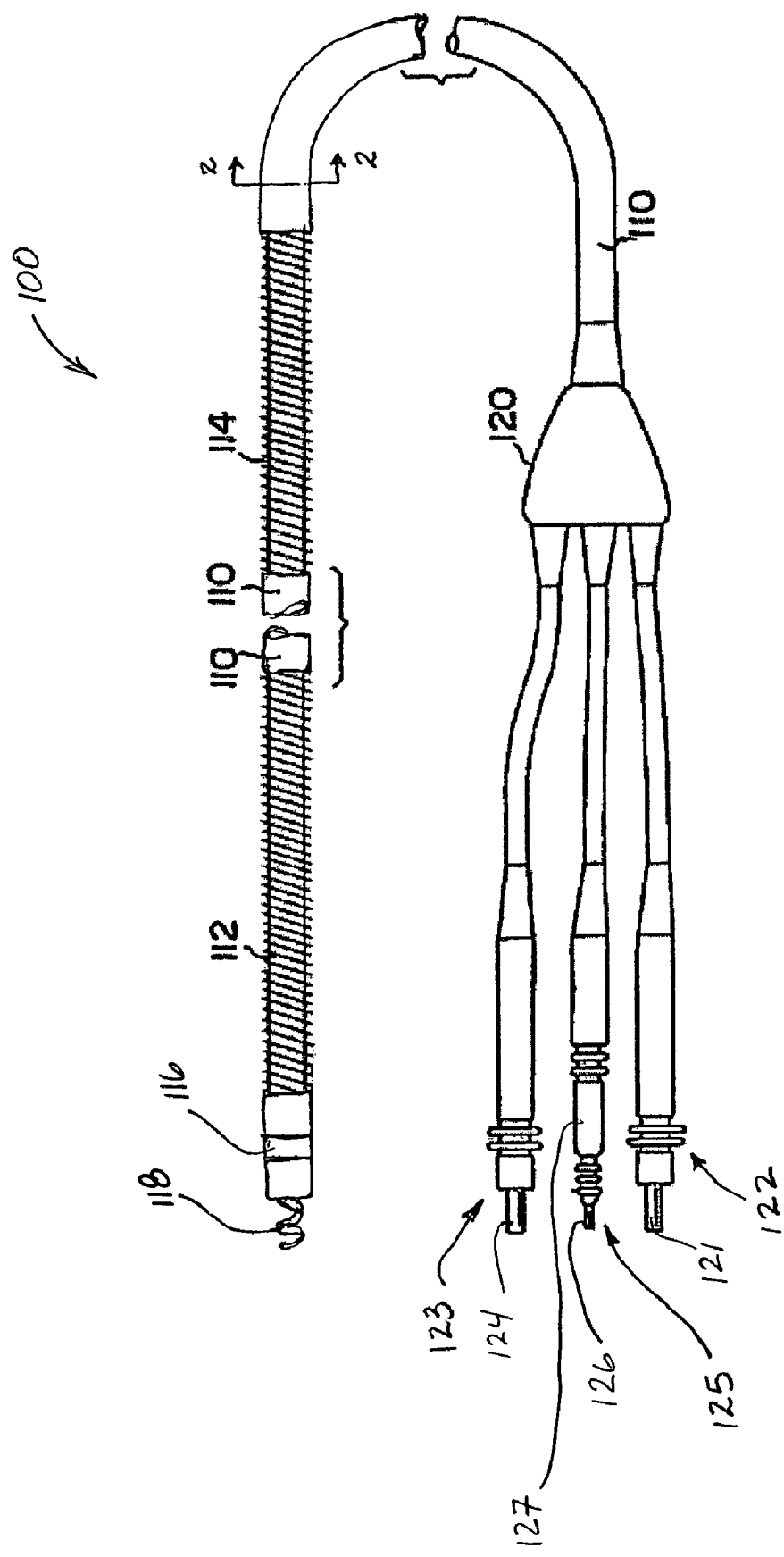
FIG. 1A is a plan view of a medical electrical lead according to one embodiment of the present invention.

The following description is exemplary in nature and is not intended to limit the scope, applicability, or configuration of the invention in any way. Rather, the following description provides a convenient illustration for implementing exemplary embodiments of the invention.

FIG. 1 is plan view of a medical electrical lead according to one embodiment of the present invention. FIG. 1 illustrates a medical electrical lead 100 including a lead body 110, a tip electrode 118, a ring electrode 116, and two defibrillation electrodes 112, 114; lead body 110 carries at least four conductors (not shown; reference FIG. 2A) to couple tip and ring electrodes 118 and 116 to a contact pin 126 and contact ring 127, respectively, of a connector leg 125 and defibrillation electrodes 112, 114 each to a contact pin 121 or 124 of a connector leg 122 or 123. Connector legs 122, 123, and 125, joined to lead body 110 via a trifurcation sleeve 120, are adapted to electrically couple lead 100 to a medical device and may each conform to an industry standard, for example DF-1 or IS-1, such as are known to those skilled in the art; configurations and constructions corresponding to connector legs 122, 123, and 125 are well known to those skilled in the art of lead construction.

According to embodiments of the present invention, lead body 110 comprises a multi-lumen tube composed of an elastomeric biocompatible and biostable insulative material, examples of which are well known to those skilled in the art and include silicone, polyurethane, and combinations thereof; one specific example of an appropriate insulative material is HP (high performance) silicone having a durometer between approximately 30 and approximately 70 on a shore A scale. FIG. 2A is a section view through section line 2-2 of FIG. 1 showing an arrangement of lumens and conductors in a multi-lumen tube 20 of lead body 110 according to one embodiment of the present invention. FIG. 2A illustrates tube 20 including a lumen 21 having an inner surface forming a substantially elliptical cross-section and a plurality of additional lumens 24A, 24B, 24C each having inner surfaces forming substantially circular cross-sections; cable conductors 12, 14, and 26 are shown positioned in lumens 24 and a coil conductor 28 positioned within lumen 21. Conductors include any suitable material known in the art of lead construction, for example an MP35N alloy, and are likewise formed according to methods known to those skilled in the art. Cable conductors 12, 14, and 26 may include insulative sheaths 27, as illustrated in FIG. 2A, each having an outer diameter between approximately 0.005 inch and approximately 0.020 inch according to embodiments of the present invention.

Figure 2A:
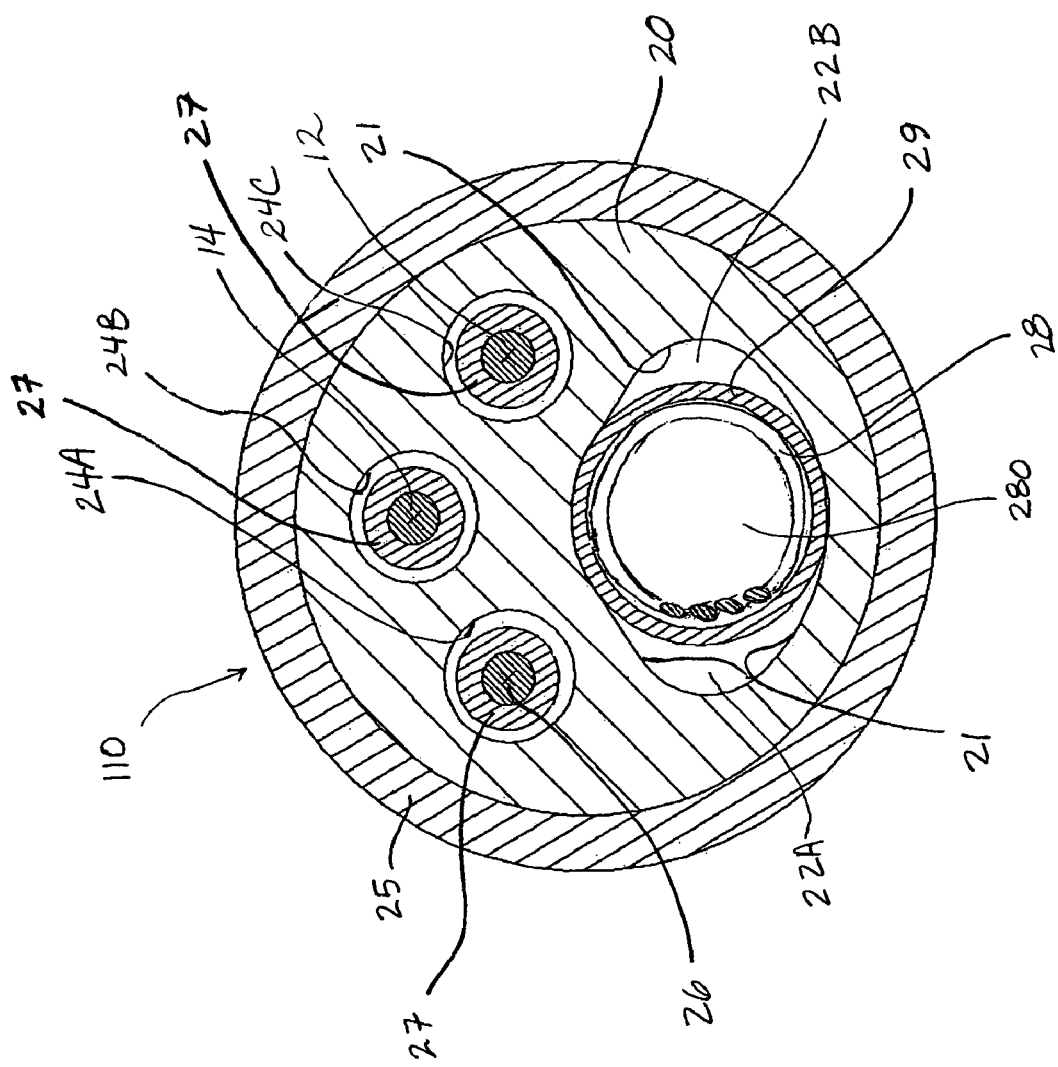
FIG. 2A is a section view through section line 2-2 shown in FIG. 1.

FIG. 2A further illustrates lead body 110 including an outer overlay sheath 25, which may be formed of a polymer such as polyurethane or silicone or a combination thereof; according to some embodiments of the present invention overlay sheath 25 is formed over multi-lumen tube 20 to make an outer diameter of lead body 110 approximately equal to that of electrodes coupled to lead body, e.g. electrodes 112, 114, and 116, illustrated in FIG. 1A; furthermore, overlay sheath 25 may have a durometer greater than that of tube 20. According to alternate embodiments of the present invention, an overlay sheath is not included.

Figure 1B:
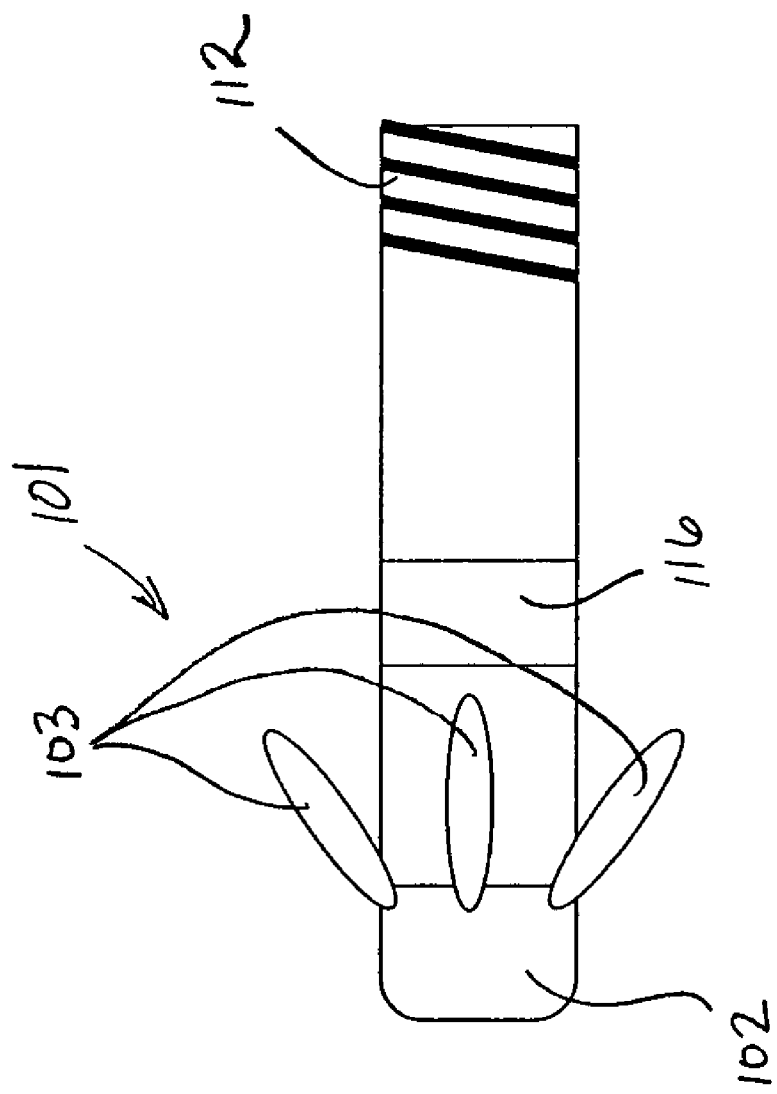
FIG. 1B is a partial plan view of an alternate distal end of the lead shown in FIG. 1A.

Referring back to FIG. 1, according to one embodiment, cable conductors 12, 14, and 26 couple each defibrillation electrode 112, 114 to contact pin 121 or 124 and ring electrode 116 to contact ring 127, while coil conductor 28 couples tip electrode 118 to contact pin 126, wherein contact pin 126 may be rotated to extend and retract tip electrode 118 into and out from lead body 110 via coil 28 by means well known to those skilled in the art of lead construction. According to an alternate embodiment coil 28 need not rotate tip electrode 118 and a tip electrode coupled to coil 28 may take an alternate form as illustrated in FIG. 1B. FIG. 1B is a partial plan view of an alternate distal end 101 of lead 100 including a tip electrode 102 and a tine structure 103 such as is commonly known to those skilled in the art.

FIG. 2A further illustrates a sheath 29 surrounding coil conductor 28, which, according to one embodiment, serves as a lubricious liner between coil 28 and inner surface of lumen 21 to facilitate efficient torque transfer from contact pin 126 and tip electrode 118; coil 28 and sheath 29 fit within lumen 21 such that two separate spaces 22A and 22B having substantially crescent-shaped cross-sections are formed. In such an embodiment, sheath 29 may be formed of a fluoropolymer such as PTFE or ETFE. According to alternate embodiments, sheath 29 may only serve as redundant insulation for coil 28, not having lubricious properties, which are not required if coil is not used to extend and retract a distal tip electrode, for example electrode 102 illustrated in FIG. 1B. In further alternate embodiments sheath 29 is not included and coil 28 alone fitted within lumen 21 may or may not have a sufficient diameter to form separate crescent-shaped spaces 22A and 22B; furthermore inner surface of lumen 21 may or may not have lubricious properties useful to facilitate extension and retraction of a tip electrode via coil 28. Coil 28 has an outer diameter between approximately 0.020 inch and approximately 0.040 inch and sheath 29 has an inner diameter between approximately 0.022 inch and approximately 0.042 inch and an outer diameter between approximately 0.026 inch and approximately 0.046 inch, according to embodiments of the present invention.

Figure 2B:
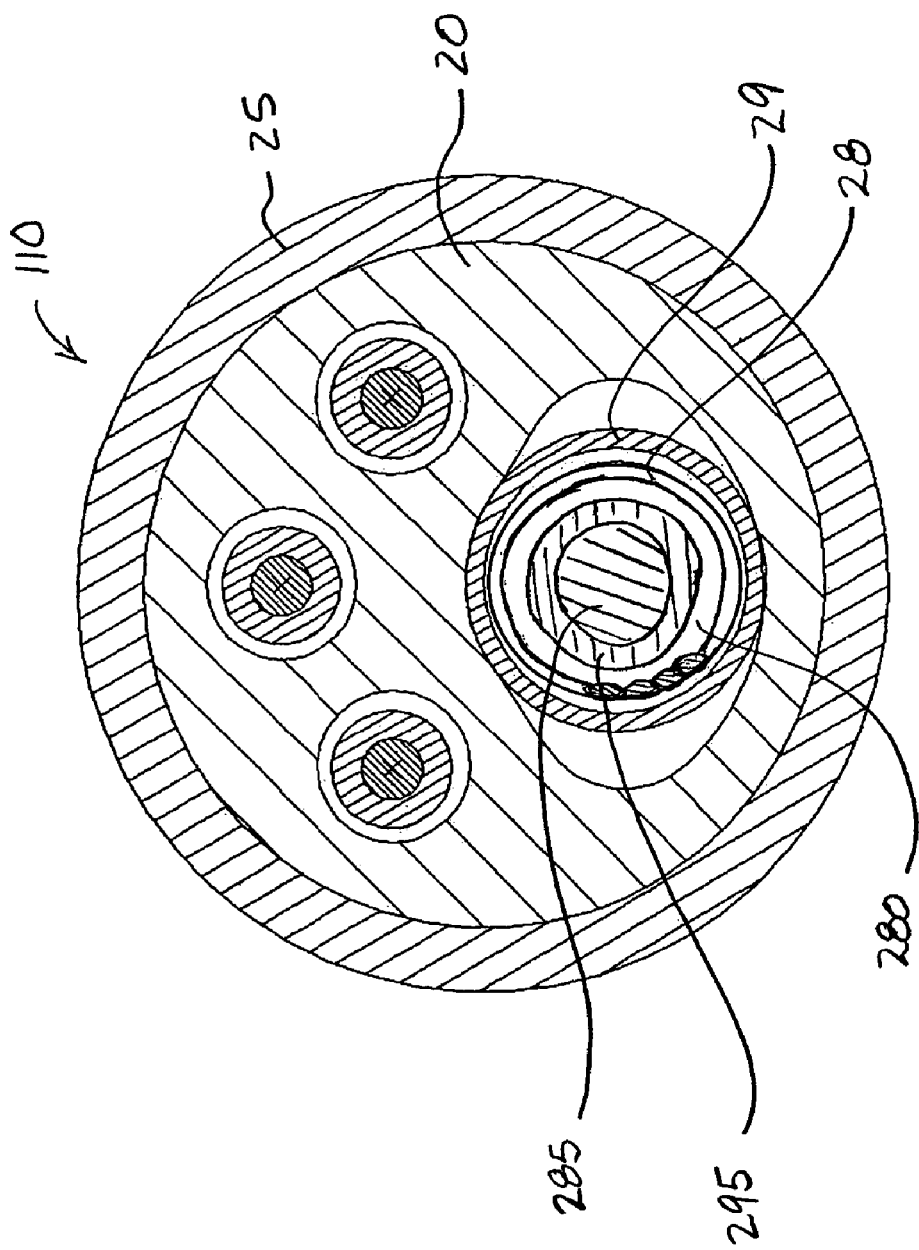
FIG. 2B is a section view of a lead body according to an alternate embodiment of the present invention.

Additional alternate embodiments further include a fifth conductor 285 extending within a lumen 280 of coil 28, as is illustrated in FIG. 2B; fifth conductor 285 is isolated from coil 28 by means of an insulative sheath 295 formed thereover. Fifth conductor 285 may be included in lead 110 to couple an additional electrode or physiological sensor to an additional contact on one of connector legs 122, 123, 125 or on an additional connector leg. It should be noted that conductors 12, 14, and 26, although illustrated having sheaths formed thereover, e.g. a sheath 27 illustrated in FIG. 2A, need not include such additional sheaths according to some embodiments of the present invention.

Figure 3:
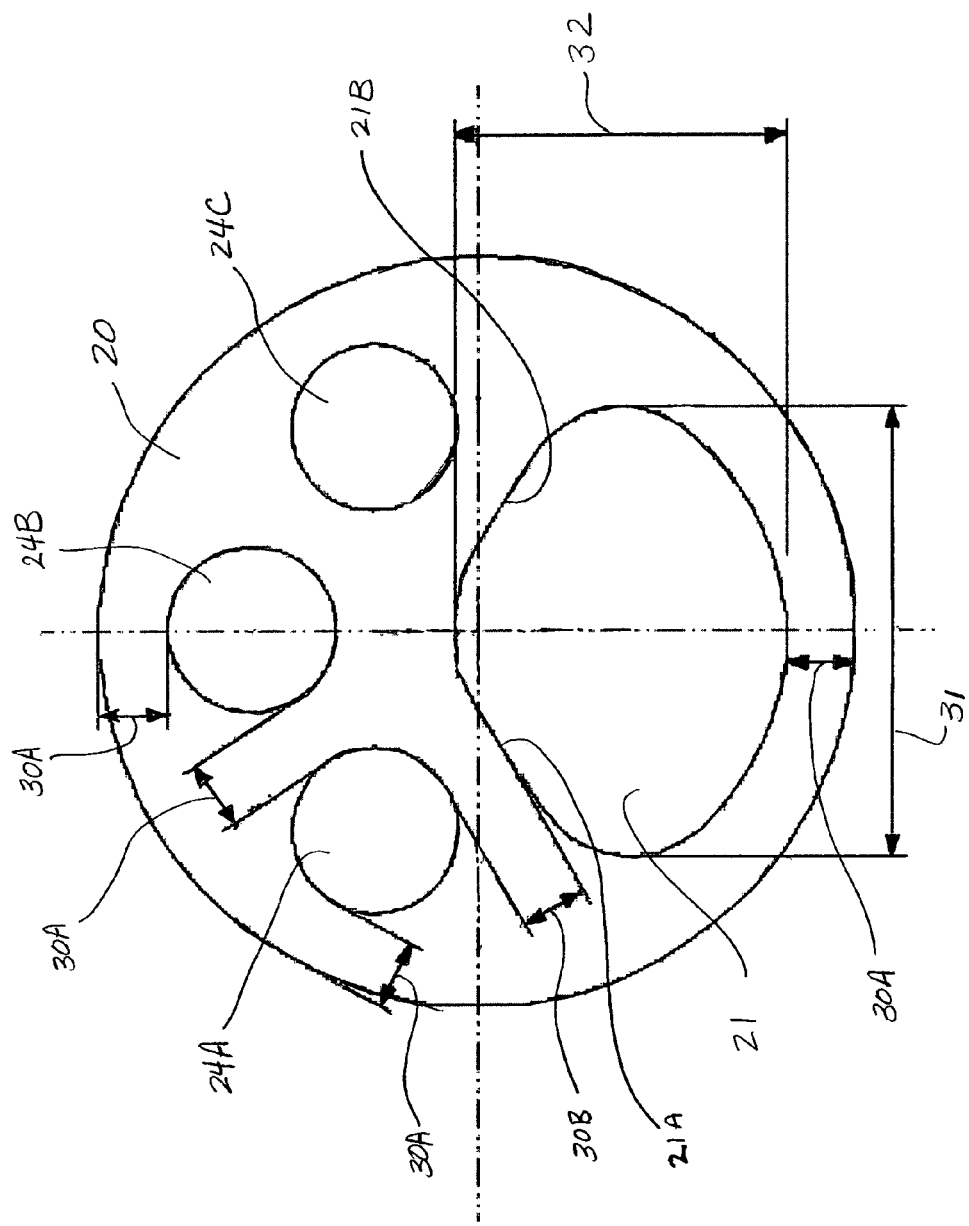
FIG. 3 is a section view of a multi-lumen tube according to an embodiment of the present invention.

As illustrated in FIG. 2A, according to one embodiment, an outer diameter of sheath 29 about coil 28 is approximately equal to or greater than a length of a minor axis of lumen 21, which is shown as item 32 in FIG. 3. FIG. 3 is a section view of multi-lumen tube 20 sans conductors. FIG. 3 illustrates inner surface of lumen 21 forming a substantially elliptical cross-section including a major axis having a length 31, which is greater than minor axis length 32; length 31 ranges between approximately 0.025 inch and 0.080 inch and length 32 ranges between 0.015 inch and 0.065 inch, according to some embodiments. Lumen 21 is positioned with respect to lumens 24A-C such that a minimum wall thickness 30A, 30B for adequate insulation is maintained between each of lumens 21, 24A-C and minimum wall thickness 30A is maintained between lumens 21 and 24A-C and an outer surface 23 of tube 20; minimum wall thicknesses 30A-B range between approximately 0.002 inch and 0.015 inch according to embodiments of the present invention. Furthermore, according to embodiments of the present invention a minimum outer diameter of tube 20 is achieved while providing the adequate insulation via the arrangement of lumens 21 and 24A-C, which are sized to accommodate appropriate conductors (reference FIGS. 2A-B); a minimum outer diameter of tube 20 ranges between approximately 0.040 inch and approximately 0.120 inch and diameters of lumens 24A-C range between approximately 0.008 inch and approximately 0.025 inch according to some embodiments. FIG. 3 further illustrates upper surfaces 21A and 21B of lumen 21 flattened, thereby creating asymmetrical portions on either side of the major axis, in order that minimum wall thickness 30B between lumens 24A and 24C and lumen 21 is maintained while maximizing space within lumen 21; such a configuration conforms herein to the term "substantially elliptical". In an alternate embodiment according to the present invention, lumen 21 is symmetrical about the major axis either being formed as an approximately 'pure' ellipse or having flattened surfaces mirroring surfaces 21A-B, both configurations conforming to the term "substantially elliptical" used herein. Lengths 31 and 32 illustrated in FIG. 3 generally correspond to relaxed dimensions or dimensions corresponding to lumen 21 in a relaxed state without a conductor disposed therein.

Figure 4:
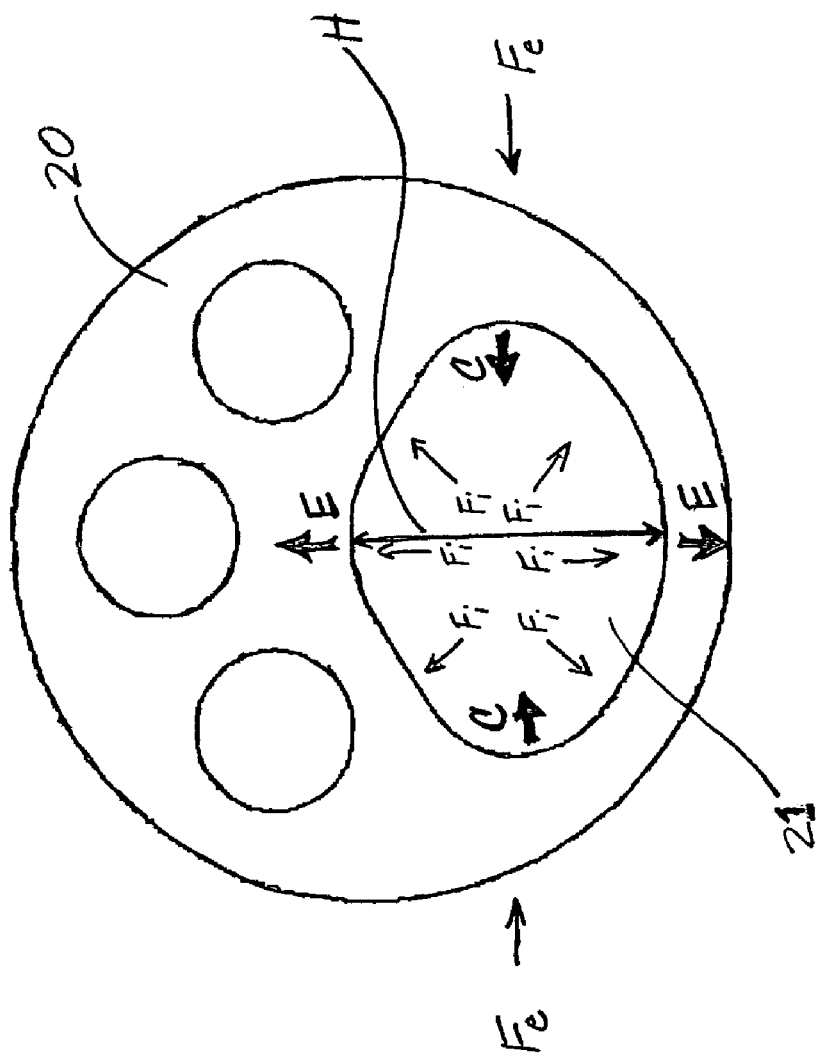
FIG. 4 is a schematic section view of a multi-lumen tube according to an embodiment of the present invention.

FIG. 4 is a schematic section view of multi-lumen tube 20 illustrating forces, which may be applied for expansion and compression of lumen 21 to accommodate a conductor. According to some embodiments of the present invention, an outer diameter of a conductor, for example conductor 28 including sheath 29 illustrated in FIGS. 2A-B, is approximately equal to or greater than a height H, corresponding to length of minor axis 32 illustrated in FIG. 3, therefore, to facilitate stringing of such a conductor into lumen 21 in a process of assembling a lead body, e.g. lead body 110, it may be necessary to expand height H of lumen 21. According to embodiments of the present invention the substantially elliptical cross-section formed by the inner surface of lumen 21 may be deformed from a relaxed state to increase height H. FIG. 4 illustrates two means for deformation: a first comprising an external force $F_e$ causing a compression C along the major axis leading to an expansion E along the minor axis and a second comprising an internal pressure increase resulting in internal forces $F_i$ likewise leading to expansion E along the minor axis. Once a conductor having an approximately equal or larger outer diameter than height H is assembled into lumen 21, height H conforms to the outer diameter of the conductor while separate substantially crescent-shaped spaces, for example spaces 22A-B illustrated in FIG. 2A, are maintained on either side of the conductor, for example conductor 28 including sheath 29 shown in FIG. 2A.

In the foregoing specification, the invention has been described with reference to specific embodiments. However, it may be appreciated that various modifications and changes can be made without departing from the scope of the invention as set forth in the appended claims. For example, the cross-sections of the lumens and the number of lumens included in the plurality of lumens illustrated herein as 24A-C may vary from that described. Furthermore, different types and numbers of conductors may be positioned within each of the lumens described herein without departing from the spirit of the present invention.

What is claimed is:

1. A medical electrical lead, comprising:
   a plurality of elongated conductors;
   a lead body having an elastomeric multi-lumen tube including an individual conductor lumen for each of the plurality of conductors, one of the individual conductor lumens including an inner surface forming a substantially elliptical cross-section, the cross-section including a minor axis having a first length in a relaxed state and being deformable such that the first length of the minor axis extends to a second length, the second length greater than the first length; and
   one of the elongated conductors extending within the substantially elliptical cross-section individual conductor lumen and including a substantially circular cross-section having an outer diameter greater than the first length, said elongated conductor contacting the inner surface to maintain the lumen in a deformed state wherein the minor axis has a length greater than the first length.

2. The lead of claim 1, further comprising a sheath formed about the conductor and including a sheath outer diameter and wherein the sheath outer diameter is approximately equal to or greater than the first length of the minor axis of the cross-section of the lumen.

3. The lead of claim 2, wherein the sheath comprises a fluoro-polymer.

4. The lead of claim 1, wherein the inner surface of the lumen is lubricious.

5. The lead of claim 1, wherein the conductor is in the form of a coil.

6. The lead of claim 5, further comprising an extendable and retractable electrode and a connector pin contact coupled to the electrode via the conductor; wherein the connector pin contact rotates the coil to extend and retract the electrode.

7. The lead of claim 5, further comprising an elongated insulated conductor and wherein the coil includes a lumen through which the insulated conductor extends.

8. The lead of claim 1, wherein the conductor is in the form of a cable.

9. The lead of claim 1, wherein the substantially elliptical cross-section of the lumen further includes a major axis dividing the cross-section into asymmetrical sections.

10. The lead of claim 1, wherein the inner surface of the lumen includes a flattened portion.

11. The lead of claim 1, wherein the tube further includes a plurality of lumens and a minimum wall thickness between each of the plurality of lumens and between each of the plurality of lumens and the lumen including a substantially elliptical cross-section is between approximately 0.002 inch and approximately 0.015 inch.

12. The lead of claim 11, wherein the minimum wall thickness is between approximately 0.002 inch and approximately 0.008 inch.

13. The lead of claim 11, wherein the tube includes a center point and wherein each of the plurality of lumens and the lumen including a substantially elliptical cross-section include a center point offset from the center point of the tube.

14. The lead of claim 11, wherein the plurality of lumens comprise three lumens.

15. The lead of claim 11, wherein each of the plurality of lumens includes an inner surface forming a substantially circular cross-section.

16. The lead of claim 11, further comprising a conductor extending within at least one of the plurality of lumens.

17. The lead of claim 1, further comprising an overlay sheath formed about the multi-lumen tube.

18. The lead of claim 17, further comprising an electrode including an outer diameter and wherein the overlay sheath includes an outer diameter approximately equal to the outer diameter of the electrode.

19. The lead of claim 1, wherein the multi-lumen tube is formed of a material comprising silicone rubber.

20. The lead of claim 1, wherein the multi-lumen tube is formed of a material comprising polyurethane.

21. The lead of claim 1, wherein the multi-lumen tube is formed of a material comprising silicone and polyurethane.

22. The lead of claim 1, wherein an intersection of the substantially circular cross-section of the conductor and the inner surface of the lumen forms two separate spaces having substantially crescent-shaped cross-sections.

23. The lead of claim 22, wherein the conductor includes a sheath formed thereover.

24. The lead of claim 23, wherein the sheath comprises a fluoro-polymer.

25. The lead of claim 22, wherein the inner surface of the lumen is lubricious.

26. The lead of claim 22, wherein the conductor is in the form of a coil.

27. The lead of claim 26, further comprising an extendable and retractable electrode and a connector pin contact coupled to the electrode via the conductor; wherein the connector pin contact rotates the coil to extend and retract the electrode.

28. The lead of claim 26, further comprising an elongated insulated conductor and wherein the coil includes a lumen through which the insulated conductor extends.

29. The lead of claim 22, wherein the conductor is in the form of a cable.

30. The lead of claim 22, wherein the substantially elliptical cross-section of the lumen further includes a major axis dividing the cross-section into asymmetrical sections.

31. The lead of claim 22, wherein the inner surface of the lumen includes a flattened portion.

32. The lead of claim 22, wherein the tube further includes a plurality of lumens and a minimum wall thickness between each of the plurality of lumens and between each of the plurality of lumens and the lumen including a substantially elliptical cross-section is between approximately 0.002 inch and approximately 0.015 inch.

33. The lead of claim 32, wherein the minimum wall thickness is between approximately 0.002 inch and approximately 0.008 inch.

34. The lead of claim 32, wherein the tube includes a center point and wherein each of the plurality of lumens and the lumen including a substantially elliptical cross-section include a center point offset from the center point of the tube.

35. The lead of claim 32, wherein the plurality of lumens comprise three lumens.

36. The lead of claim 32, wherein each of the plurality of lumens includes an inner surface forming a substantially circular cross-section.

37. The lead of claim 32, further comprising a conductor extending within at least one of the plurality of lumens.

38. The lead of claim 22, further comprising an overlay sheath formed about the multi-lumen tube.

39. The lead of claim 38, further comprising an electrode including an outer diameter and wherein the overlay sheath includes an outer diameter approximately equal to the outer diameter of the electrode.

40. The lead of claim 22, wherein the multi-lumen tube is formed of a material comprising silicone rubber.

41. The lead of claim 22, wherein the multi-lumen tube is formed of a material comprising polyurethane.

42. The lead of claim 22, wherein the multi-lumen tube is formed of a material comprising silicone and polyurethane.

* * * * *